(12) United States Patent
Wu et al.

(10) Patent No.: US 11,524,978 B2
(45) Date of Patent: Dec. 13, 2022

(54) SYNTHETIC PEPTIDES, PHARMACEUTICAL COMPOSITIONS COMPRISING THE SAME, AND USES THEREOF IN TREATING THROMBOEMBOLISM-RELATED DISEASES

(71) Applicant: Academia Sinica, Taipei (TW)

(72) Inventors: Han-Chung Wu, Taipei (TW); Yuan-Sung Kuo, Taipei (TW)

(73) Assignee: ACADEMIA SINICA, Taipei (TW)

( * ) Notice: Subject to any disclaimer, the term of this patent is extended or adjusted under 35 U.S.C. 154(b) by 400 days.

(21) Appl. No.: 16/823,356

(22) Filed: Mar. 19, 2020

(65) Prior Publication Data

US 2020/0299329 A1    Sep. 24, 2020

Related U.S. Application Data

(60) Provisional application No. 62/821,982, filed on Mar. 21, 2019.

(51) Int. Cl.
*C07K 7/06* (2006.01)
*A61K 47/64* (2017.01)
*A61K 38/43* (2006.01)

(52) U.S. Cl.
CPC .............. *C07K 7/06* (2013.01); *A61K 38/43* (2013.01); *A61K 47/64* (2017.08)

(58) Field of Classification Search
None
See application file for complete search history.

(56) References Cited

PUBLICATIONS

Davison, S.P., et al. 2004 Plast ReconstrSurg 114: 43e-51e. (Year: 2004).*
Falanga, A., et al. 2005 Annals of Oncology 16: 696-701. (Year: 2005).*
Thachil, J. 2012 Blood Reviews 26: 175-181. (Year: 2012).*
Carrier, M., et al. 2013 J Thromb Haemost 11: 1760-1765. (Year: 2013).*

* cited by examiner

*Primary Examiner* — Marsha Tsay (57) ABSTRACT

Disclosed herein is a biomolecule comprising a synthetic peptide for targeting thrombus, a pharmaceutical composition comprising the same, and uses thereof in the treatment of thromboembolism-related diseases. According to embodiments of the present disclosure, the synthetic peptide having the amino acid sequence of SEQ ID NO: 1, 2, or 3 exhibits a binding affinity and specificity to thrombus. Thus, the synthetic peptide may serve as a targeting element for delivering a therapeutic agent (e.g., an anticoagulant agent or a thrombolytic agent) to the thrombus thereby improving the therapeutic safety and efficacy of the therapeutic agent.

16 Claims, 9 Drawing Sheets

Specification includes a Sequence Listing.

Before

After

SEQUENCE LISTING

```
<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: Synthetic

<400> SEQUENCE: 1

Phe Gln Asn Glu Trp Phe His Asn Phe Leu His Asp
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic

<400> SEQUENCE: 2

Thr Glu Ala Asn Leu Ser Ser Trp Val Phe Ala Arg
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic
```

```
<400> SEQUENCE: 3

Leu Gln Lys Asn Pro Phe Asp Leu Val Gln Ile Leu
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Synthetic

<400> SEQUENCE: 4

Gly Gly Gly Gly Ser
1               5
```

SYNTHETIC PEPTIDES, PHARMACEUTICAL COMPOSITIONS COMPRISING THE SAME, AND USES THEREOF IN TREATING THROMBOEMBOLISM-RELATED DISEASES

BACKGROUND OF THE INVENTION

1. Field of the Invention

The present disclosure in general relates to the field of disease treatment. More particularly, the present disclosure relates to three synthetic peptides and uses thereof in the treatment of thromboembolism-related diseases.

2. Description of Related Art

Thrombosis is the formation of thrombus (also known as blood clot) within a blood vessel or cardiac chamber. It is a common pathology underlying various thromboembolism-related diseases, including ischemic heart disease (e.g., angina, myocardial infarction, and sudden cardiac death), ischemic stroke, and venous thromboembolism (VTE). According to the World Health Organization (WHO), myocardial infraction and stroke are the top two causes of death globally that collectively cause 25 percent of deaths worldwide. Therefore, research on the molecular mechanism and treatment of thromboembolism-related diseases is of crucial importance.

The mainstay of treatment for thromboembolism-related diseases includes surgery, anticoagulant therapy, and thrombolysis. However, all the treatments cannot produce a satisfactory effect on thromboembolism-related diseases due to the limitations of harmful side-effects. For example, surgery may result in bleeding, wound haematoma, infection, and/or nerve damage; while anticoagulant therapy and thrombolysis are reported to induce off-target effect that causes life-threatening bleeding.

In view of the foregoing, there exists in the related art a need for a novel method for treating thromboembolism-related diseases in a more safe and efficient manner.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a biomolecule comprising a synthetic peptide for targeting thrombus. According to embodiments of the present disclosure, the synthetic peptide has an amino acid sequence of FQNEWFHNFLHD (SEQ ID NO: 1), TEANLSSWVFAR (SEQ ID NO: 2), or LQKNPFDLVQIL (SEQ ID NO: 3).

Optionally, the present biomolecule further comprises a signal peptide disposed at and connected to the upstream of the synthetic peptide.

According to preferred embodiments, the present biomolecule further comprises a therapeutic agent coupled to the synthetic peptide, wherein the therapeutic agent is an anticoagulant agent or a thrombolytic agent. Examples of the anticoagulant agent include, but are not limited to, coumarin, warfarin, acenocoumarol, phenprocoumon, atromentin, phenindione, brodifacoum, difenacoum, heparin, fondaparinux, idraparinux, idrabiotaparinux, rivaroxaban, apixaban, edoxaban, betrixaban, darexaban, letaxaban, eribaxaban, hirudin, lepirudin, bivalirudin, argatroban, dabigatran, ximelagatran, batroxobin, hementin, coumadin, aspirin, ticlopidine, clopidogrel, and prasugrel. Exemplary thrombolytic agent include, tissue plasminogen activator (tPA; for example reteplase, alteplase, tenecteplase, or lanoteplase), staphylokinase, streptokinase, or urokinase According to certain embodiments of the present disclosure, the biomolecule further comprises a linker, which comprises glycine (G) and serine (S) residues. In these embodiments, the therapeutic agent is coupled to the synthetic peptide via the linker. According to one working example, the linker comprises the amino acid sequence of GGGGS (SEQ ID NO: 4).

Optionally, the biomolecule further comprises a reporter molecule coupled to the synthetic peptide or the therapeutic agent. Depending on desired purposes, the reported molecule may be a tag molecule, a radioactive molecule, a fluorescent molecule, a phosphorescent molecule, or a chemiluminescent molecule.

Also disclosed herein is a pharmaceutical composition or medicament for treating thrombosis or a thromboembolism-related disease. The pharmaceutical composition or medicament of the present disclosure comprises the present biomolecule, and a pharmaceutically acceptable excipient, in which the biomolecule comprises a synthetic peptide and a therapeutic agent coupled thereto.

Another aspect of the present disclosure pertains to a method of preventing and/or treating thrombosis or a thromboembolism-related disease in a subject in need thereof. The method comprises administering to the subject an effective amount of the biomolecule, the pharmaceutical composition, or the medicament in accordance with any aspect or embodiment of the present disclosure.

The subject treatable with the present biomolecule, pharmaceutical composition, or medicament is a mammal; preferably, a human.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIGS. 1A-1B depict the results for screening phage clones targeting human thrombus according to one embodiment of the present disclosure.

FIGS. 1C-1D depict the binding affinity of the selected phage clones for the indicated proteins according to one embodiment of the present disclosure.

FIGS. 2A-2C depicts the targeting ability of specified peptides toward a thrombus in vivo according to another example of the present disclosure.

FIG. 4 depicts the analytic results of peptide-tPA fusion proteins according to another example of the present disclosure. Panel A are photographs of gel electrophoresis analyzing the expression of specified fusion proteins. Panel B are photographs of western blot confirming the expression of specified fusion proteins. Wild-type tPA served as a positive control in this experiment. Panel C is a line chart depicting the cleavage activity of specified fusion proteins. tPA activity was assayed by use of Z-Gly-Gly-Arg-AMC as a fluorometric substrate. Upon specific cleavage, the substrate becomes fluorescent with excitation at 380 nm and emission at 420 nm. Y-axis EX380/EM420, fluorescence emission arbitrary units.

FIGS. 5A-5B depict the results of the infrared fluorescence imaging of mice treated with specified fusion proteins.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

The term "peptide" refers to a polymer of amino acids without regard to the length of the polymer. This term also does not specify or exclude chemical or post-expression modifications of the peptides of the invention, although chemical or post-expression modifications of these peptides may be included or excluded as specific embodiments. Therefore, for example, modifications to peptides that include the covalent attachment of glycosyl groups, acetyl groups, phosphate groups, lipid groups and the like are expressly encompassed by the term peptide. Further, peptides with these modifications may be specified as individual species to be included or excluded from the present invention. Throughout the present disclosure, the positions of any specified amino acid residues within a peptide are numbered starting from the N terminus of the peptide. When amino acids are not designated as either D- or L-amino acids, the amino acid is either an L-amino acid or could be either a D- or L-amino acid, unless the context requires a particular isomer. Further, the notation used herein for the peptide amino acid residues are those abbreviations commonly used in the art.

As used herein, the term "synthetic peptide" refers to a peptide which does not comprise an entire naturally occurring protein molecule. The peptide is "synthetic" in that it may be produced by human intervention using such techniques as phage-display techniques, chemical synthesis, recombinant genetic techniques, or fragmentation of whole antigen or the like.

As discussed herein, minor variations in the amino acid sequences of peptides are contemplated as being encompassed by the presently disclosed and claimed inventive concept(s), providing that the variations in the amino acid sequence maintain at least 70% sequence identity, such as at least 70%, 71%, 72%, 73%, 75%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% sequence identity. Peptides of the present disclosure may be modified specifically to alter a feature of the peptide unrelated to its physiological activity. For example, certain amino acids can be changed and/or deleted without affecting the physiological activity of the peptide in this study (i.e., its ability to target thrombus). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the peptide derivative. Fragments or analogs of proteins/peptides can be readily prepared by those of ordinary skill in the art. Preferred amino- and carboxy-termini of fragments or analogs occur near boundaries of functional domains. In one example, one amino acid residue (e.g., valine) of the present synthetic peptide is conservatively replaced (e.g., by leucine). In other examples, two amino acid residues of the present synthetic peptide are conservatively replaced by other suitable amino acid residues, for example, valine (V) and arginine (R) are replaced by the pair of amino acids that includes, but is not limited to, methionine (M) and lysine (K), lysine (K) and proline (P), tryptophan (W) and isoleucine (I), isoleucine (I) and proline (P), asparagine (N) and valine (V), and glutamine (G) and lysine (K).

"Percentage (%) sequence identity" is defined as the percentage of amino acid residues in a candidate sequence that are identical with the amino acid residues in the specific peptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNAS-TAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). The percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$\frac{X}{Y} \times 100$$

where X is the number of amino acid residues scored as identical matches by the sequence alignment program BLAST in that program's alignment of A and B, and where Y is the total number of amino acid residues in A or B, whichever is shorter.

The term "administered", "administering" or "administration" are used interchangeably herein to refer a mode of delivery, including, without limitation, intraveneously, intramuscularly, intraperitoneally, intraarterially, intracranially, or subcutaneously administering a biomolecule, pharmaceutical composition or medicament comprising the peptide of the present invention. In some embodiments, the biomolecule comprising the peptide of the present invention is mixed with a suitable excipient (e.g., buffer solution) before use, such as intraveneous injection.

As used herein, the term "treat," "treating" and "treatment" are interchangeable, and encompasses partially or completely preventing, ameliorating, mitigating and/or managing a symptom, a secondary disorder or a condition associated with thrombus. The term "treating" as used herein refers to application or administration of one or more biomolecule of the present disclosure to a subject, who has a symptom, a secondary disorder or a condition associated with thrombus, with the purpose to partially or completely alleviate, ameliorate, relieve, delay onset of, inhibit progression of, reduce severity of, and/or reduce incidence of one or more symptoms, secondary disorders or features associated with thrombus. Symptoms, secondary disorders, and/or conditions associated with thrombus include, but are not limited to, angina, myocardial infarction, sudden cardiac death, ischemic stroke, and venous thromboembolism (VTE). Treatment may be administered to a subject who exhibits only early signs of such symptoms, disorder, and/or condition for the purpose of decreasing the risk of developing the symptoms, secondary disorders, and/or conditions associated with thrombus. Treatment is generally "effective" if one or more symptoms or clinical markers are reduced as that term is defined herein. Alternatively, a treatment is "effective" if the progression of a symptom, disorder or condition is reduced or halted.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., biomolecule of the present disclosure), such as molar concentration, mass concentration, volume concentration, molality, mole fraction, mass fraction and mixing ratio. Persons having ordinary skills could calculate the human equivalent dose (HED) for the medicament (such as the present biomolecule) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The phrase "pharmaceutically acceptable" refers to molecular entities and compositions that are "generally regarded as safe," e.g., that are physiologically tolerable and do not typically produce an allergic or similar untoward reaction, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "excipient" as used herein means any inert substance (such as a powder or liquid) that forms a vehicle/carrier for the active agent. The excipient is generally safe, non-toxic, and in a broad sense, may also include any known substance in the pharmaceutical industry useful for preparing pharmaceutical compositions such as, fillers, diluents, agglutinants, binders, lubricating agents, glidants, stabilizer, colorants, wetting agents, disintegrants, and etc.

The term "subject" refers to a mammal including the human species that is treatable with the biomolecule, pharmaceutical composition, medicament and/or method of the present invention. The term "subject" is intended to refer to both the male and female gender unless one gender is specifically indicated.

II. Description of the Invention

The present disclosure is based, at least in part, on the discovery that three synthetic peptides respectively comprising the amino acid sequences of FQNEWFHNFLHD (SEQ ID NO: 1), TEANLSSWVFAR (SEQ ID NO: 2), and LQKNPFDLVQIL (SEQ ID NO: 3) exhibit a binding affinity and specificity to thrombus. Thus, the present disclosure aims at providing a biomolecule comprising the synthetic peptide, and uses thereof in treating thrombus.

According, the first aspect of the present is directed to a biomolecule comprising a synthetic peptide, which has the amino acid sequence at least 85% (i.e., 85%, 86%, 87%, 88%, 89%, 90%, 91%, 92%, 93%, 94%, 95%, 96%, 97%, 95%, 99% or 100%) identical to SEQ ID NO: 1, 2, or 3. According to working examples of the present disclosure, the synthetic peptide comprises the amino acid sequence 100% identical to SEQ ID NO: 1, 2, or 3.

The synthetic peptides of the invention can be produced by any commonly used method, such as phage-display technique (i.e., biopanning of phage-display peptides for selecting a desired peptide exhibiting binding affinity to a target molecule), or t-BOC or FMOC protection of alpha-amino groups (i.e., stepwise syntheses whereby a single amino acid is added at each step starting from the C terminus of the peptide). Peptides of the invention can also be synthesized by the well-known solid phase peptide synthesis methods. Alternatively, the synthetic peptide of the invention can be produced by host cells (e.g., HEK293 cells), which is transfected with a nucleic acid encoding the peptide.

For the purpose of providing a therapeutic effect, the present biomolecule may further comprises a therapeutic agent coupled to the synthetic peptide. According to some embodiments of the present disclosure, the therapeutic agent is an anticoagulant agent or a thrombolytic agent. Examples of anticoagulant agent suitable to be employed in the present biomolecule include, but are not limited to, coumarin, warfarin, acenocoumarol, phenprocoumon, atromentin, phenindione, brodifacoum, difenacoum, heparin, fondaparinux, idraparinux, idrabiotaparinux, rivaroxaban, apixaban, edoxaban, betrixaban, darexaban, letaxaban, eribaxaban, hirudin, lepirudin, bivalirudin, argatroban, dabigatran, ximelagatran, batroxobin, hementin, coumadin, aspirin, ticlopidine, clopidogrel, and prasugrel. Regarding the thrombolytic agent, it may be any of tPA (e.g., reteplase, alteplase, tenecteplase, or lanoteplase), staphylokinase, streptokinase, or urokinase. As would be appreciated, the therapeutic agent may alternatively be other molecules, which exhibit a prophylactic and/or therapeutic effect on thrombus (e.g., inhibiting the formation of thrombus, or dissolving the occluding thrombus), for example, fibrinolytic agents or antiplatelet agents. According to certain working examples, the therapeutic agent is tPA.

Optionally, the synthetic peptide and the therapeutic agent is coupled via a linker. According to some embodiments of the present disclosure, the amino acid sequence of the linker comprises a plurality of glycine (G) and/or serine (S) residues. In one specific embodiment, the linker comprises the amino acid sequence of GGGGS (SEQ ID NO: 4).

Still optionally, the present biomolecule may further comprise a reporter molecule coupled to the synthetic peptide or the therapeutic agent. Depending on intended purposes, the reporter molecule may be a tag molecule (e.g., chitin binding protein (CBP), maltose binding protein (MBP), glutathione-S-transferase (GST), thioredoxin (TRX), strep tag, FLAG™ tag, Myc tag, human influenza hemagglutinin (HA) tag, or polyhistidine (His) tag), a radioactive molecule (e.g., Gallium-67, Molybdenum-99, Indium-111, or Thallium-201), a fluorescent molecule (e.g., green fluorescent protein (GFP), cyan fluorescent protein (CFP), blue fluorescent protein (BFP), yellow fluorescent protein (YFP), or the enhanced variants thereof), a phosphorescent molecule (e.g., europium-, dysprosium-, or terbium-doped lutetium orthophosphate, strontium aluminate, or strontium magnesium silicate; copper-activated zinc sulphide; silver-activated zinc sulphide; copper-activated zinc-cadmium sulphide; or bismuth-activated calcium-strontium sulphide), or a chemiluminescent molecule (e.g., coelenterazine, lucigenin, luciferin, luciferase, or an oxalate in combination with a dye). According to one embodiment of the present disclosure, the present biomolecule comprises a Myc tag coupled to the therapeutic agent. According to another embodiment of the present disclosure, the present biomolecule comprises a His tag coupled to the therapeutic agent. According to still another embodiment of the present disclosure, the present biomolecule comprises a Myc tag coupled to the therapeutic agent, and a His tag coupled to the Myc tag.

According to some working examples, the biomolecule is in the form of a fusion protein. In these examples, a signal peptide is disposed at and connected to the upstream of the synthetic peptide of the present disclosure so as to direct or enhance the expression or secretion of the synthetic peptide. The signal peptide may be a natural or a synthetic signal peptide. According to one specific example, the signal peptide is derived from mouse immunoglobulin (IG) kappa. The fusion protein of the present disclosure comprises in sequence, i.e., from N-terminus to C-terminus, a signal peptide, a synthetic peptide, a linker, a therapeutic agent, a Myc tag, and a His tag.

Also disclosed herein are the uses of the present biomolecule in the preparation of a medicament or a pharmaceutical composition for the treatment of thrombosis or thromboembolism-related diseases. The medicament or pharmaceutical composition comprises a biomolecule of the present disclosure, and a pharmaceutically acceptable excipient, in which the biomolecule comprises a synthetic peptide and a therapeutic agent coupled to the synthetic peptide. Preferably, the therapeutic agent is an anticoagulant agent or a thrombolytic agent.

In general, the present biomolecule is present in the medicament or pharmaceutical composition at a level of about 0.01% to 99.9% by weight, based on the total weight of the medicament or pharmaceutical composition. In some embodiments, the present biomolecule is present in the medicament or pharmaceutical composition at a level of at least 0.1% by weight, based on the total weight of the medicament or pharmaceutical composition. In certain embodiments, the present biomolecule is present in the medicament or pharmaceutical composition at a level of at least 5% by weight, based on the total weight of the medicament or pharmaceutical composition. In still other embodiments, the present biomolecule is present in the medicament or pharmaceutical composition at a level of at least 10% by weight, based on the total weight of the medicament or pharmaceutical composition. In still yet other embodiments, the present biomolecule is present in the medicament or pharmaceutical composition at a level of at least 25% by weight, based on the total weight of the medicament or pharmaceutical composition.

The medicament or pharmaceutical composition may comprise different types of excipients or carriers depending on the intended routes of administration. The present medicament or pharmaceutical composition may be administered intraveneously, intradermally, intraarterially, intraperitoneally, intralesionally, intracranially, intranasally, intrapleurally, intratracheally, intrarectally, topically, intramuscularly, subcutaneously, intravascularly, intrapericardially, intraocularly, orally, topically, locally, injection, inhalation, infusion, localized perfusion, in any suitable forms such as powders, creams, liquids, aerosols and etc.

In some embodiments, the medicament or pharmaceutical compositions of this disclosure are solid dosage forms for oral administration. Such solid dosage forms may be capsules, sachets, tablets, pills, lozengens, powders or granules. In such forms, the active ingredient such as any of the biomolecules described above is mixed with at least one pharmaceutically acceptable excipient. Any of the described solid dosage forms may optionally contain coatings and shells, such as enteric coatings, and coatings for modifying the release rate of any of the ingredients. Examples of such coatings are well known in the art. In one example, the medicaments or pharmaceutical compositions of this disclosure are tablets such as quick-release tablets. In still another example, the medicaments or pharmaceutical compositions of this disclosure are formulated into sustained release forms. In another example, the medicaments or pharmaceutical compositions of this disclosure are powders that are encapsulated in soft and hard gelatin capsules.

In some embodiments, the medicaments or pharmaceutical compositions of the present disclosure are liquid dosage forms for oral administration. The liquid formulation may further include a buffering agent to maintain a desired pH. The liquid dosage formulations may also be filled into soft gelatin capsules. For example, the liquid may include a solution, suspension, emulsion, micro-emulsion, precipitate or any desired liquid media carrying any of the biomolecules as described above, or a pharmaceutically acceptable derivative, salt or solvate thereof, or a combination thereof. The liquid may be designed to improve the solubility of active biomolecules as described above to form a drug-containing emulsion or disperse phase upon release.

In some embodiments, the medicaments or pharmaceutical compositions of this disclosure are formulations suitable for parenteral administration, such as administration by injection, which includes, but is not limited to, subcutaneous, bolus injection, intramuscular, intraperitoneal and intravenous injection. The medicaments or pharmaceutical compositions may be formulated as isotonic suspensions, solutions or emulsions in oily or aqueous vehicles, and may contain formulary agents such as suspending, stabilizing or dispersing agents. Alternatively, the compositions may be provided in dry form such as powders, crystallines or freeze-dried solids with sterile pyrogen-free water or isotonic saline before use. They may be presented in sterile ampoules or vials.

When the present biomolecule is formulated to be administered by intravenous, cutaneous or subcutaneous injection, the peptide will be in the form of a pyrogen-free, parenterally acceptable aqueous solution. The preparation of such parenterally acceptable polypeptide solutions, having due regard to pH, isotonicity, stability, and the like, is within the skill in the art. A preferred medicament or pharmaceutical composition for intravenous, cutaneous, or subcutaneous injection should contain, in addition to the present biomolecule, an isotonic vehicle such as Sodium Chloride Injection, Ringer's Injection, Dextrose Injection, Dextrose and Sodium Chloride Injection, Lactated Ringer's Injection, or other vehicle as known in the art. The medicament or pharmaceutical composition of the invention may also contain stabilizers, preservatives, buffers, antioxidants, or other additives known to those of skill in the art. The duration of intravenous therapy using the medicament or pharmaceutical composition of the invention will vary, depending on the severity of the disease being treated and the condition and potential idiosyncratic response of each individual subject. It is contemplated that the duration of each application of the present biomolecule will be in the range of 12 to 24 hours of continuous intravenous administration. Ultimately the attending physician will decide on the appropriate duration of intravenous therapy.

The present biomolecule may also be formulated into physiologically acceptable form suitable for topically, systematically, or locally administration. For example, the present biomolecule may be applied on the surface of an implant or device. Further, the composition may desirably be encapsulated or injected in a viscous form for delivery to thrombus. Additional useful agents may also optionally be included in the medicament or pharmaceutical composition, as described above, or may be administered simultaneously or sequentially with the medicament or pharmaceutical composition of the invention.

Another aspect of the present disclosure pertains to a method of preventing and/or treating thrombosis or a thromboembolism-related disease in a subject in need thereof by use of the present biomolecule, which comprises a synthetic peptide and a therapeutic agent coupled thereto. The method comprises administering to the subject an effective amount of said biomolecule, or a medicament or pharmaceutical composition comprising the same.

The effective amount of the present biomolecule, medicament of pharmaceutical composition may vary with many factors, such as the particular condition being treated, the severity of the condition, the individual patient parameters (including age, physical condition, size, gender and weight), the duration of the treatment, the nature of concurrent therapy (if any), the specific route of administration and like factors within the knowledge and expertise of the health practitioner.

In one embodiment, the subject is a mouse. To elicit a therapeutic effect in mice, about 0.1 to 100 mg/Kg (e.g., 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/Kg) body weight per dose of the present biomolecule is administered; preferably, about 0.5 to 50 mg/Kg body weight per dose of the present biomolecule is administered; more preferably, about 1 to 20 mg/Kg body weight per dose of the present biomolecule is administered. According to one working example, 2 to 10 mg of the present biomolecule per Kg body weight per dose is sufficient to elicit a therapeutic effect (e.g., diminishing the volume of thrombus, or recovering the blood flow) in the subject.

A skilled artisan could calculate the human equivalent dose (HED) of the present biomolecule, based on the doses determined from animal models. Accordingly, the effective amount of the present biomolecule suitable for use in a human subject may be in the range of 10 µg/Kg to 10 mg/Kg (e.g., 10, 20, 30, 40, 50, 60, 70, 80, 90, 100, 150, 200, 250, 300, 350, 400, 450, 500, 550, 600, 650, 700, 750, 800, 850, 900, or 950 µg/Kg, or 1, 2, 3, 4, 5, 6, 7, 8, 9, or 10 mg/Kg) body weight per dose for human; preferably, 50 µg/Kg to 5 mg/Kg body weight per dose; more preferably, the effective HED is about 100 to 1,000 µg/Kg per dose.

As would be appreciated, the present method can be applied to the subject, alone or in combination with additional therapies that have some beneficial effects on the prophylaxis or treatment of thrombosis or a thromboembolism-related disease. Depending on the intended purpose, the present method can be applied to the subject before, during, or after the administration of the additional therapies.

The thromboembolism-related disease may be an ischemic heart disease (e.g., myocardial infarction), limb ischemia, venous thromboembolism (VTE, including deep vein thromboembolism (DVT) and pulmonary embolism (PE)), arterial thromboembolism (ATE), neoplasia, hemolytic anemia, inflammation, sepsis, hyperadrenocorticism, cerebrovascular disease (e.g., stroke), or other diseases or conditions associated with/caused by thrombosis.

A further aspect of the present disclosure is directed to a method of determining the presence or location of a thrombus or embolus in a subject in need thereof (e.g., a subject having or suspected of having a thrombus or an embolus) by use of the present biomolecule, which comprises a synthetic peptide and a reporter molecule coupled thereto. The method comprises administering to the subject an sufficient amount of said biomolecule, and detecting the signal of the report molecule thereby determining the present or location of the thrombus or embolus.

According to certain working examples of the present disclosure, the subject is a mouse, in which about 1 to 20 mg/Kg body weight per dose of the present biomolecule is administered to the mouse so as to determining the presence and location of a thrombus. A skilled artisan may readily determine the HED of the present biomolecule, based on the doses determined from animal studies provided in working examples of this application.

In addition to the mouse and human, the subject may alternatively be other mammals, for example, a rat, a hamster, a guinea pig, a rabbit, a dog, a cat, a cow, a goat, a sheep, a monkey, and a horse.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods
Phage Display Biopanning
A human thrombus was isolated and collected from a cadaver about 20 years ago in a course of fresh cadaver dissection and partial thrombus was grounded to powder and then incubated with $2 \times 10^{11}$ phages in 1% BSA in PBS at 4° C. for 1 hour. After washing with PBS, the bound phages were eluted from the thrombus tissue and amplified using *E. coli* for subsequent rounds of selection. The eluted and amplified phages were titrated on lysogeny broth (LB) medium plates containing isopropyl β-D-1-thiogalactopyranoside (IPTG) and X-Gal (5-bromo-4-chloro-3-indolyl-D-galactoside). The biopanning steps described above were repeated five times before phage clones were randomly selected for thrombus ELISA screening.

Screening of Thrombus-Binding Activity of Phages by ELISA

The grinded human thrombus tissue or BSA in coating buffer was used to coat 96-well ELISA plates overnight. After blocking and washing, the selected phage clones were added and incubated for 1 hour at room temperature (RT). After washing with PBS, each well was probed with horseradish peroxidase (HRP)-conjugated mouse anti-M13 antibodies (1:2000 dilution) for 1 hour at RT. After repeating the wash step, the plates were developed with ELISA substrate solution. The reaction was terminated with 3N hydrochloric acid, and the absorbance of the colorimetric substrate was analyzed using a microplate reader at 450 nm.

Flow Cytometry Analysis

Mice whole blood was collected and HUVEC cells ($2 \times 10^5$ to $2 \times 10^6$ cells) were incubated with the selected phages ($5 \times 10^9$ to $5 \times 10^{10}$ pfu) at 4° C. for 1 hour. The samples were then incubated with anti-M13 monoclonal antibody at 4° C. for 1 hour, followed by FITC- or PE-conjugated anti-mouse Fab Abs at 4° C. for 30 minutes. The fluorescence profile was analyzed by flow cytometry. FITC and PE were excited with a 488 nm laser, and fluorescence emission was measured using a green channel filter (530/30) and yellow channel filter (585/42), respectively.

In Vivo Homing Experiment

Mice were anesthetized and a thrombus was induced by insertion of a paper soaked in 10% $FeCl_3$ into the right jugular for 5 to 10 minutes. The mice were then injected intravenously with $5 \times 10^9$ pfu phages. After a 10 minute incubation, the mice were sacrificed and perfused with 50 ml PBS to remove unbound phages. Organs and thrombus were harvested, and phages in the samples were titered with *E. coli* cells on IPTG/X-Gal plates. Furthermore, the thrombus and organs were embedded in optimal cutting temperature (O.C.T.) compound to prepare sections for immunohistochemistry.

Immunohistochemical Staining

The tissue samples from the in vivo phage homing experiments were sliced and placed on slides, O.C.T was removed, and samples were fixed with 4% paraformaldehyde before incubation with 1% BSA for 30 minutes to block non-specific binding. After washing, the sections were incubated with mouse anti-M13 antibodies at a dilution of 1:250 for 1 hour, followed by treatment with polymer-based SUPER SENSITIVE™ IHC detection system. In brief, the sections were incubated with Super Enhancer reagent for 20 minutes and poly-HRP reagent for 30 minutes. DAB was used as a chromogen to visualize peroxidase activity, and the samples were counterstained with hematoxylin, mounted with mounting medium, and examined by light microscopy.

Construction, Expression and Purification of tPA and Peptide-tPA Fusion

The human recombinant tPA and peptide-fusion tPA were cloned into the expression vector. The plasmids were individually transfected into 293 cells, and the transfected cells were continuously incubated in serum-free medium at 37° C. for 1 week to produce recombinant proteins. Next, the culture medium was harvested, centrifuged and passed through a 0.45-μm filter membrane. The protein in the supernatant was purified by column chromatography. After dialyzing the product with PBS, purified proteins were examined by SDS-PAGE with Coomassie blue staining. The concentration of proteins was assessed.

Activity of tPA and Targeting Peptide-tPA Fusion

To measure tPA protein activity in a fluorometric kinetic ELISA, 5 ng/μl tPA or targeting peptide-tPA fusion were mixed with 100 μM Z-Gly-Gly-Arg-AMC peptide substrate in assay buffer (50 mM Tris, 0.01% Tween-20, pH 8.5). The enzyme activity was measured by a fluorescence spectrophotometer with 380 nm excitation and 460 nm emission.

Localization of tPA and Targeting Peptide-tPA Fusion in Thrombus

Fifty micrograms of tPA or targeting peptide-tPA fusion and 4 nM HILYTE FLUOR™ 750 were mixed for 45 minutes at RT to promote conjugation. The solution was dialyzed with a 3.5-kDa-cut-off membrane overnight at 4° C. Time-course fluorescence measurements were made in mice with thrombi after intravenous injection of HILYTE FLUOR™ 750-labeled tPA or targeting peptide-tPA fusion protein. Fluorescence images were captured using an imaging system. Accumulation of HILYTE FLUOR™ 750 in the thrombus was quantified by subtracting background florescence intensity.

In Vivo Infrared Fluorescence Imaging of Living Mice

Fifty micrograms of thrombus affinity peptide-tPA was mixed with 4 nM HILYTE FLUOR™ 750 and incubated for 45 minutes at RT in the dark to promote the conjugation. Dialysis was performed with a 3.5-kDa-cut-off membrane overnight at 4° C. to remove excess dye. A time-course of infrared fluorescence images were acquired after intravenous injection of HILYTE FLUOR™ 750-conjugated fusion protein or tPA. Infrared fluorescence images of HILYTE FLUOR™ 750-conjugated protein were captured in living using an imaging system. Accumulation of HILYTE FLUOR™ 750 fluorescence signal in the induced thrombus was quantified and analyzed by software.

Measurement of Bloodflow with Laser Doppler Flowmetry

The mice were placed in a supine position on a warming pad at 37° C. and anesthetized with isoflurane. Measurement of blood flow over thrombosis of the right external jugular vein was performed 20 minutes before injection of tPA or targeting peptide-tPA fusion (2-10 mg/kg). The blood flow was then assessed using a laser Doppler scanner just before the injection of tPA or targeting peptide-tPA fusion and throughout the duration of the experiment.

Measurement of Bloodflow with Echo Sensor

Measurement of blood flow over thrombosis of the right internal carotid artery was performed. The mice were anesthetized with avertin before surgery and maintained with isoflurane. Color Doppler was performed to analyze blood flow before the injection of tPA or targeting peptide-tPA fusion (2-10 mg/kg) and throughout the duration of the experiment.

MCAO Model and Magnetic Resonance Imaging (MRI)

A murine MCAO model was established with minor modifications. In short, 10-week-old C57BL/6 mice were weighed and anesthetized with 10% isoflurane. The skin of the anterior neck was incised to expose the common carotid artery, internal carotid artery and external carotid artery, which were then separated from the vagus nerve. A vessel clip was placed upstream of the common carotid artery bifurcation and a small inlet was made on the internal carotid artery. A nylon suture was used to obstruct the middle carotid artery for 45 minutes, after which the suture was removed. The success of the model was confirmed by laser Doppler flowmetry, and the blood flow in the internal carotid artery in the brain was decreased by more than 30%. Mouse brains were imaged 24 h post-drug delivery by a bore horizontal MRI system. Contrast T2-weighted spin echo images were taken (TR=400 ms, TE=10.8 ms, FOV=2×2 cm, NEX=8, slice thickness 0.8 mm). The SNR was calculated by dividing the signal of ROI (mean pixel intensity) by the standard deviation of the background noise.

Figure 1A:
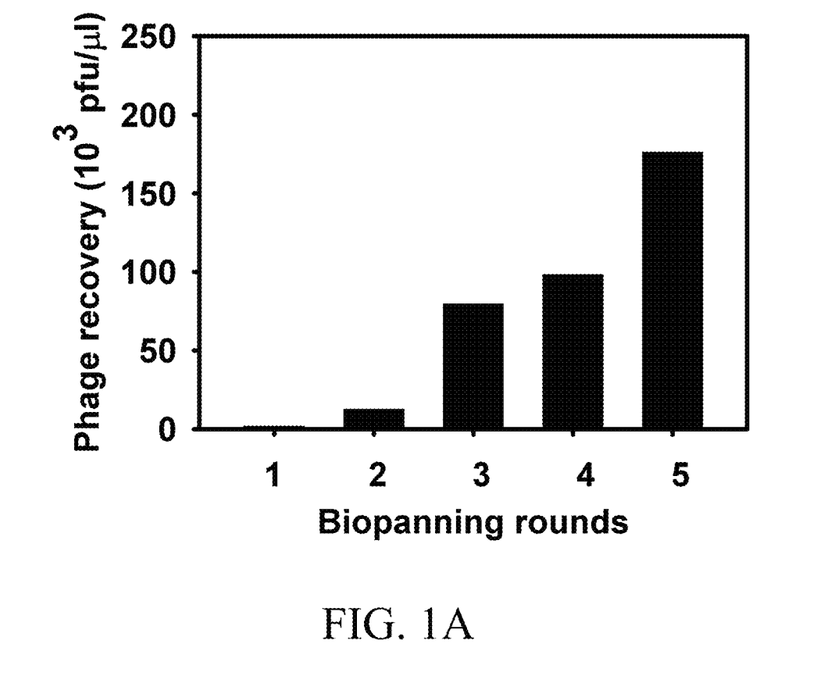
FIG. 1A is a histogram illustrating the titers of eluted phages from different rounds of biopanning.
Figure 1B:
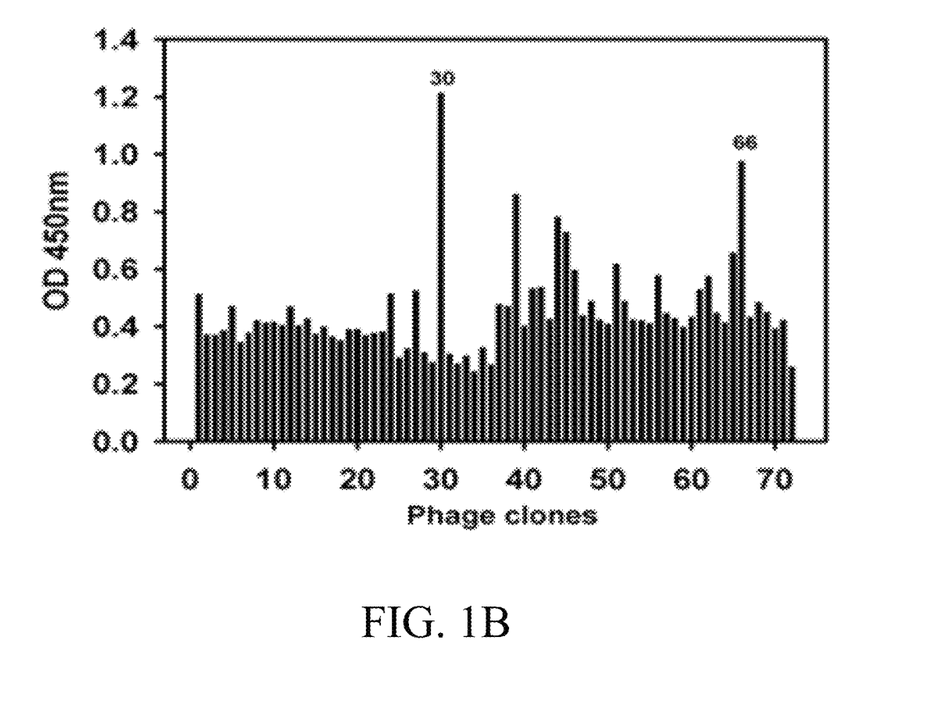
FIG. 1B is the data of enzyme-linked immunosorbent assay (ELISA) that illustrates the binding affinity of specified phages and human thrombus. Y-axis, absorption at 450 nm.
Figure 1C:
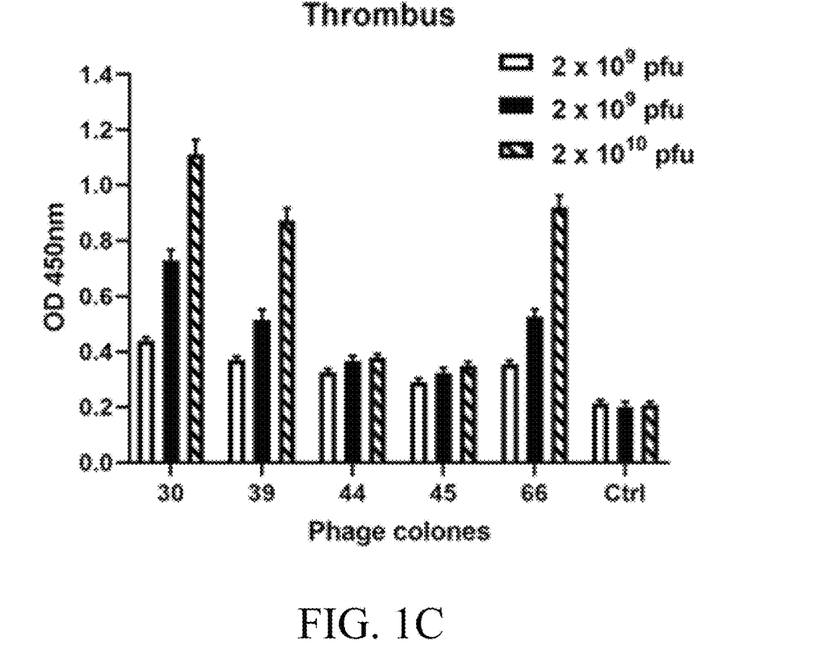
FIG. 1C is the ELISA data depicting specified phages bind to thrombus in a dose-dependent manner.
Figure 1D:
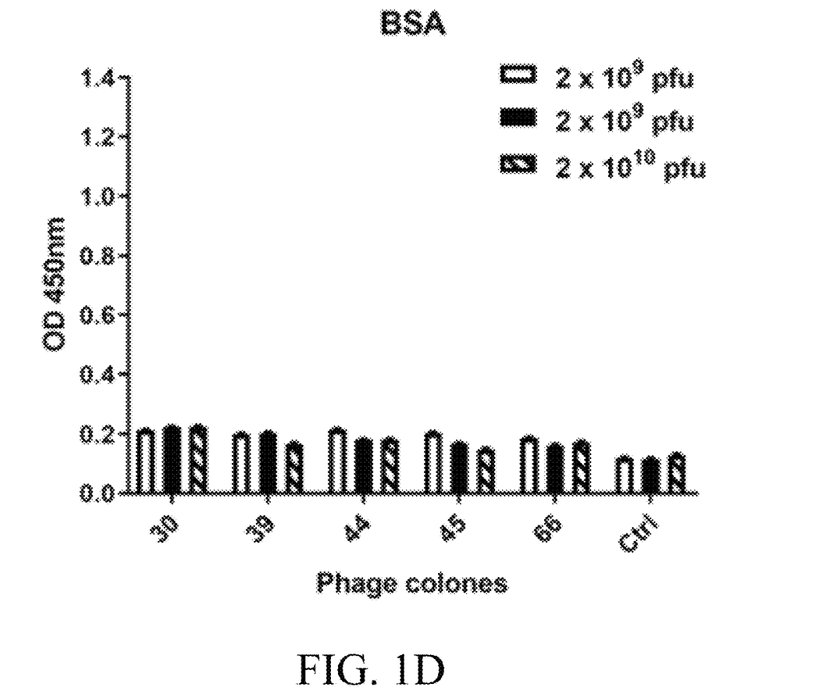
FIG. 1D is the ELISA data depicting the binding affinity of specified phages to bovine serum albumin (BSA), which serves as a negative control in this experiment.

Example 1 Identification and Characterization of Novel Peptides 1.1 Selecting Novel Peptides by Phage Display Technique To identify peptides that specifically target thrombosis, a phage display peptide library was employed to select peptides that bind to the thrombus. After five rounds of biopanning, the titer of thrombus-bound phage was increased up to 106-fold (FIG. 1A). Screening of 72 phage clones from the fifth round of biopanning was conducted, and phage clones PC30, PC39, PC44, PC45 and PC66 were selected based on their relatively high binding affinity (FIG. 1B). To avoid selecting peptides that non-specifically bind to non-thrombus tissue, whole blood cells and HUVECs were used as negative controls for counter-selection by flow cytometry (data not shown). Analysis of dose-dependent binding by ELISA revealed that phage clones PC30 (FQNEWFHNFLHD; SEQ ID NO: 1), PC39 (TEANLSSWVFAR; SEQ ID NO: 2) and PC66 (LQKNPFDLVQIL; SEQ ID NO: 3) exhibited the best thrombus-specific binding (FIG. 1C) using BSA binding as a negative control (FIG. 1D).

1.2 In Vivo Verification of Binding Activity of Selected Peptides

Figure 2A:
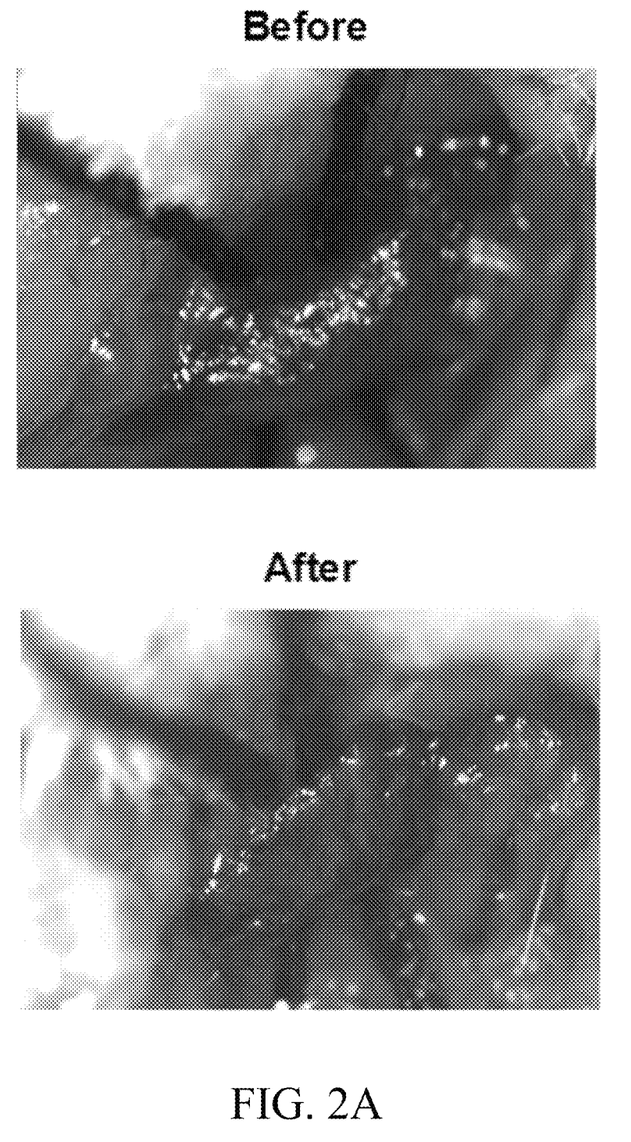
FIG. 2A are photographs of the right jugular vein of mice before (left photograph) and after (right photograph) inducing a thrombus.
Figure 2B:
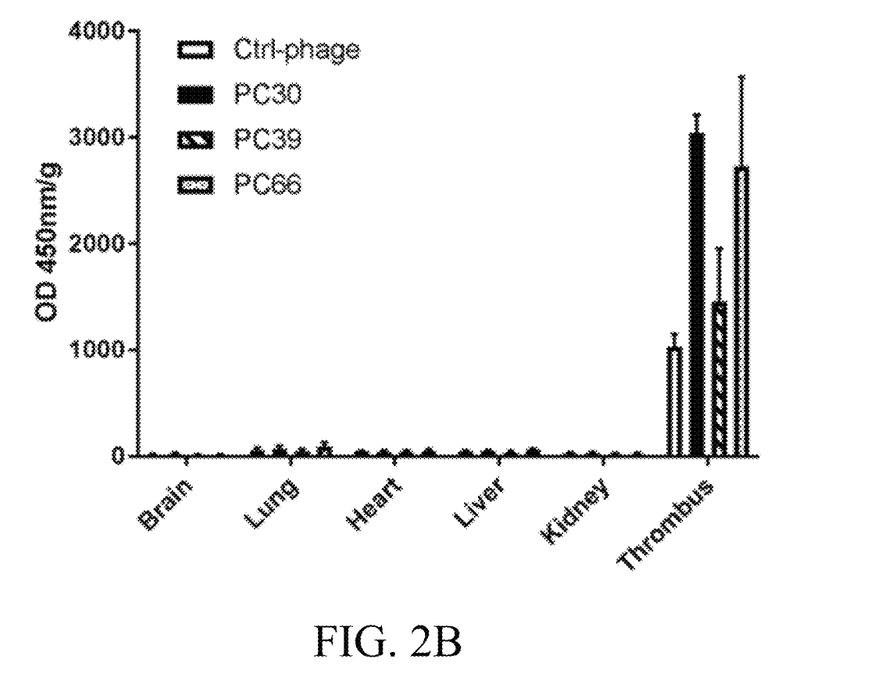
FIG. 2B is the ELISA result of the tissue distribution of specified phages. Y-axis, absorption at 450 nm.
Figure 2C:
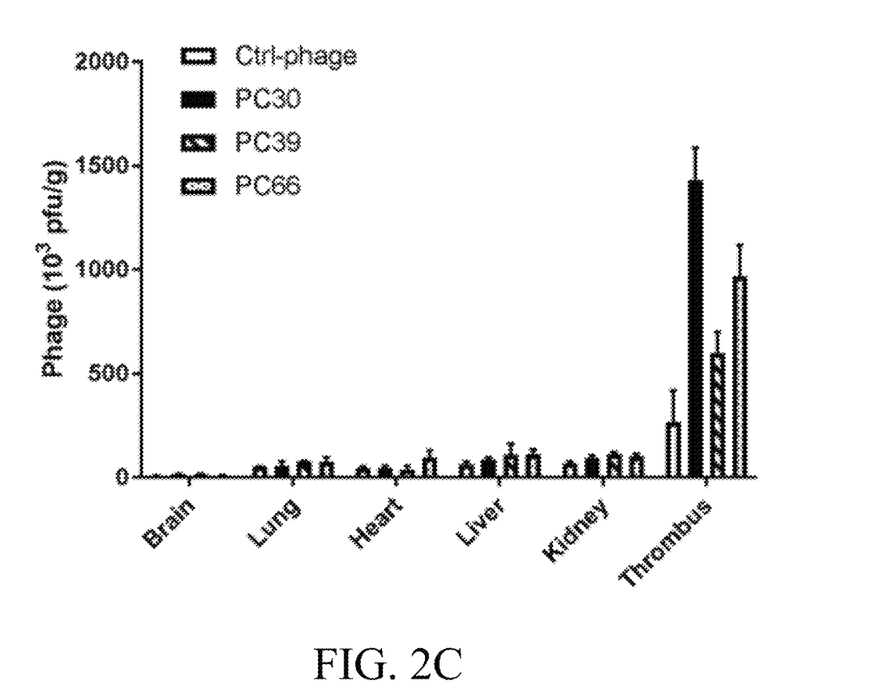
FIG. 2C is the result of phage titer assay that illustrates the tissue distribution of specified phages.
Figure 3:
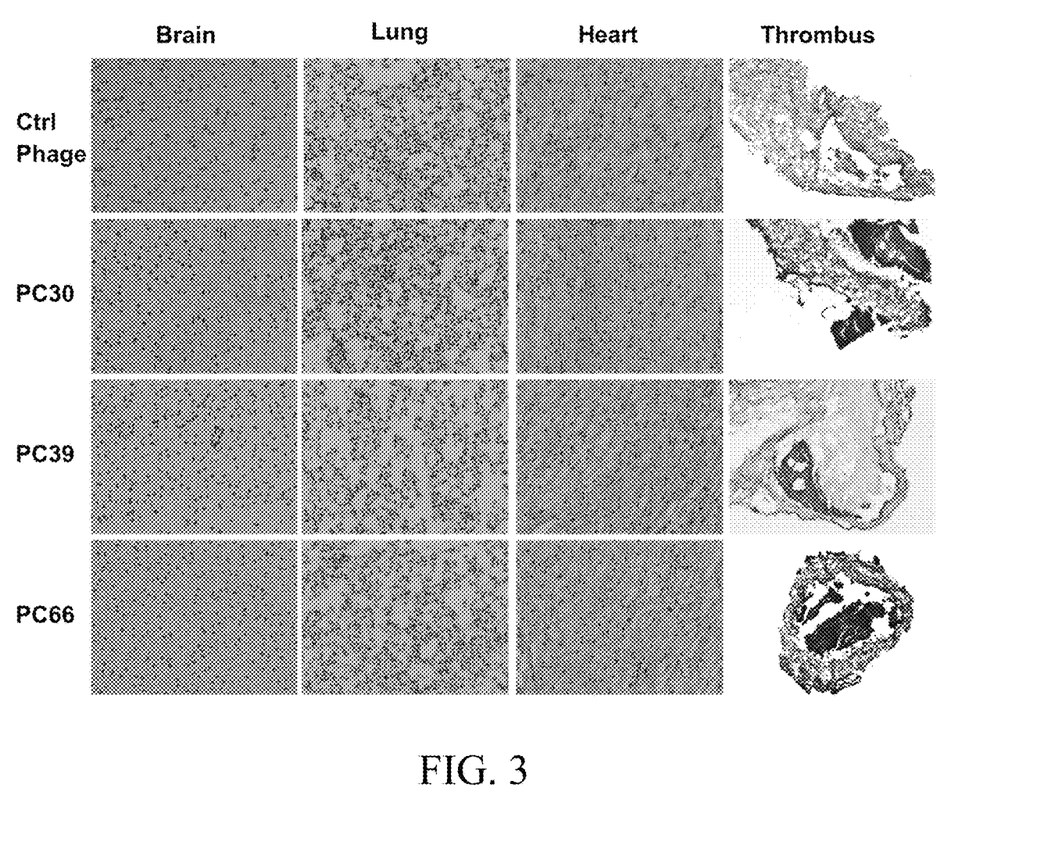
FIG. 3 is the photographs of immunohistochemistry (IHC) according to one embodiment of the present disclosure, in which compared to the negative control, the specified phages specifically bind to the thrombus in vivo.

To characterize the thrombus binding of the three selected phages in vivo, the phages selected in Example 1.1 were injected into mice with thrombi that were induced in the right jugular vein (FIG. 2A). ELISA (FIG. 2B) and a phage titer assay (FIG. 2C) revealed that the phages were highly accumulated in the induced thrombus, while organs such as brain, lung, heart liver and kidney showed low levels of non-specific phage binding. Immunohistochemistry confirmed the selected phages were exclusively located in thrombus and were not detectable in normal organs (FIG. 3).

Example 2 Generation and Characterization of SP30/SP66-tPA Fusion Protein 2.1 Preparing Fusion Proteins To target tPA specifically to the thrombus in vivo, a fusion protein was constructed in this example. From N- to C-terminal, the fusion comprised a secretion signal from mouse Ig kappa, a selected thrombus-binding peptide (from PC30 or PC66), a flexible glycine-rich linker (GGGGS), tPA, a myc tag for detection, and a His tag for purification. The thrombus-targeting peptides from PC30 and PC66 phage clones are hereafter designated as SP30 and SP66, respectively.

After expression and purification, fusion proteins were characterized by gel electrophoresis. The data of coomassie blue staining (Panel A of FIG. 4) and immunoblotting with antisera specific for tPA (Panel B of FIG. 4) indicated that the two thrombus-specific binding peptide fusion proteins migrated similarly without visible differences in electrophoresis.

Figure 4:
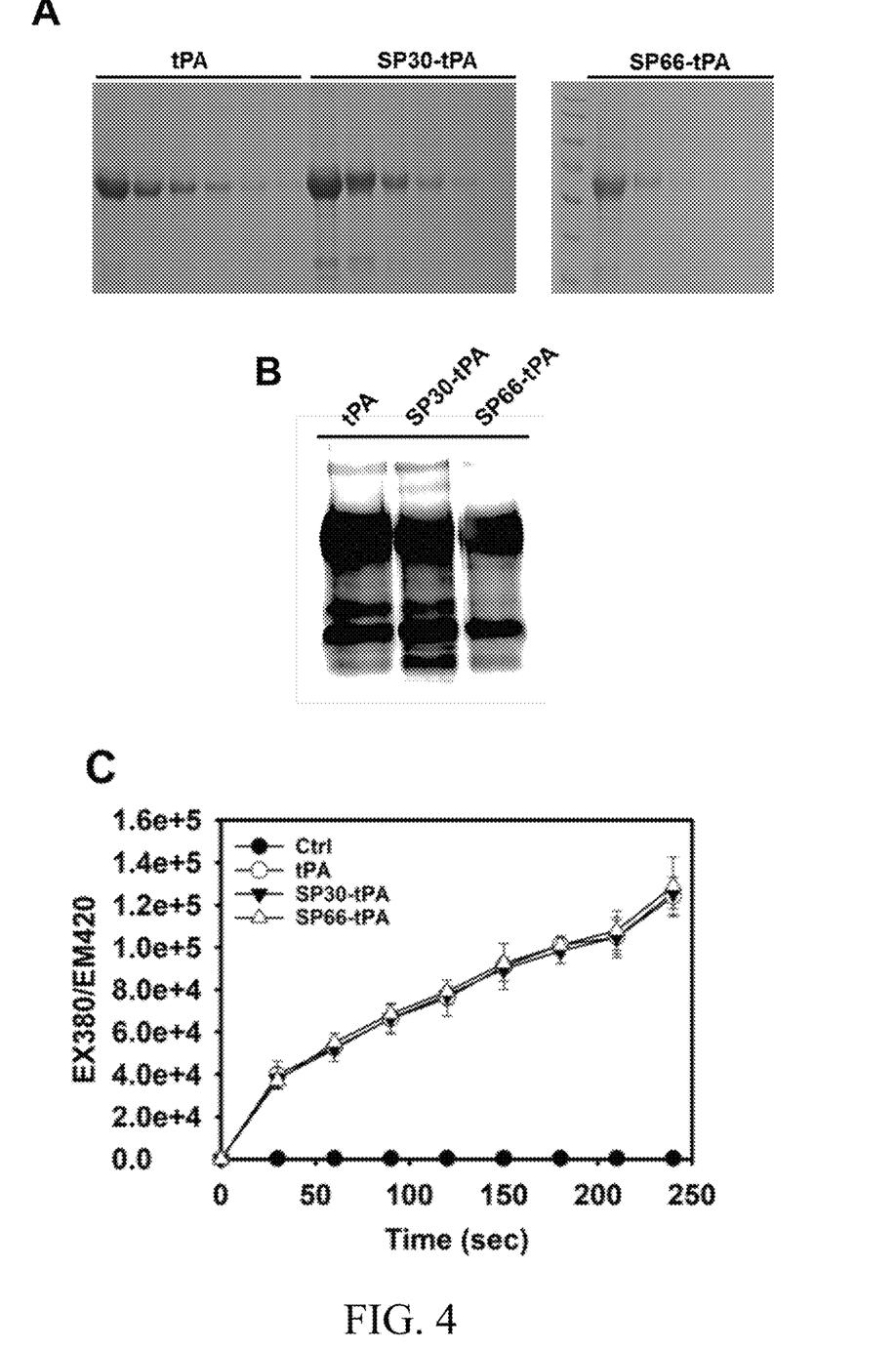

Next, an enzyme activity assay using the Z-Gly-Gly-Arg-AMC substrate was performed to confirm that the addition of thrombus affinity peptide did not diminish tPA activity. The enzyme activity assay revealed that addition of the thrombus-binding peptide did not affect tPA activity (Panel C of FIG. 4C).

2.2 Biodistribution of SP30/SP66-tPA at Thrombus In Vivo

An infrared fluorescence probe (HILYTE FLUOR™ 750) was conjugated to SP30-tPA and SP66-tPA in this example so as to directly monitor the localization of SP30/SP66-tPA and the local concentrations in living mice.

Figure 5A:
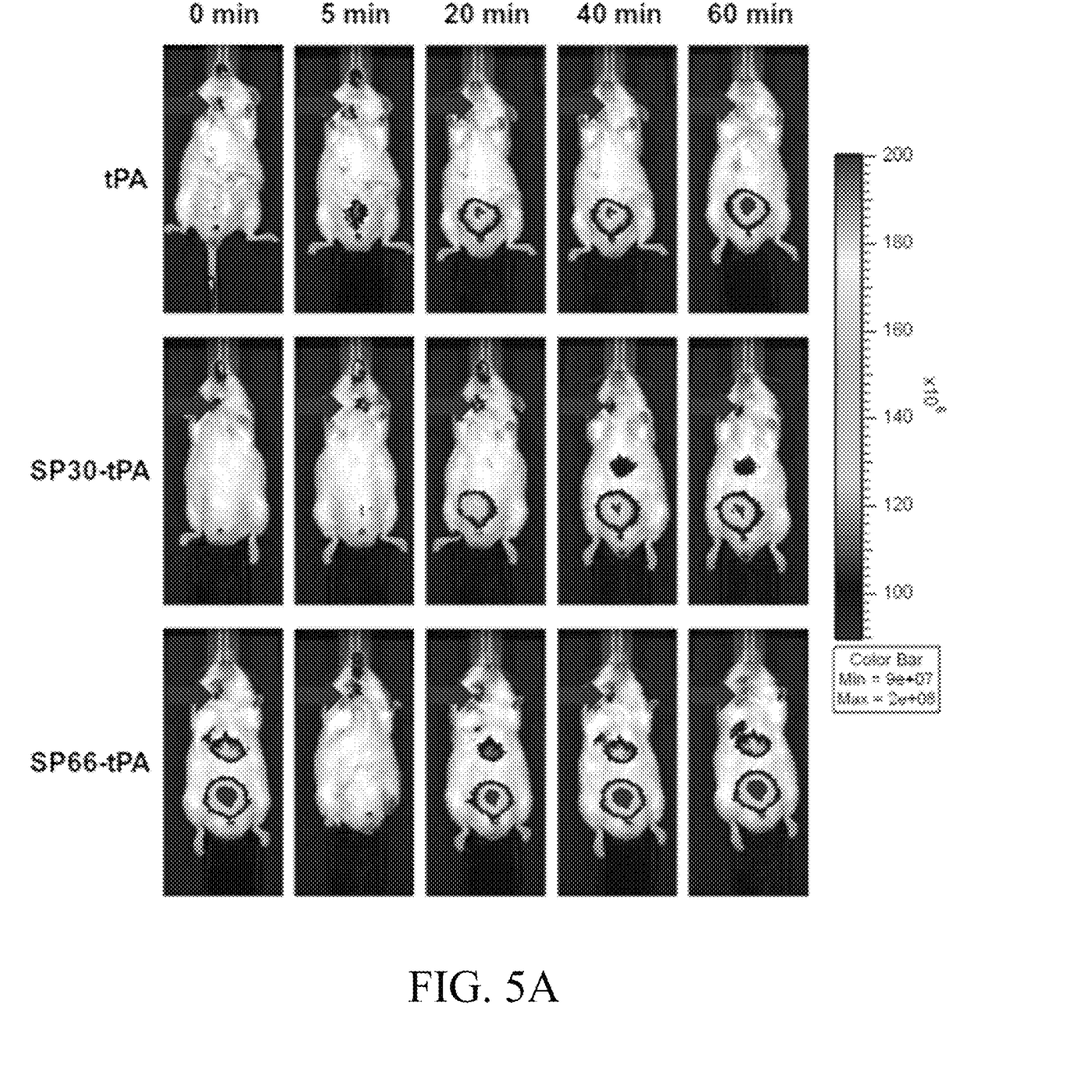
FIG. 5A are photographs infrared fluorescence images taken at 0 minutes, 5 minutes, 20 minutes, 40 minutes and 1 hour post-treatment. The most intense infrared fluorescence signal was located at the right external jugular vein, near the neck. The arrow indicates the induced thrombus.
Figure 5B:
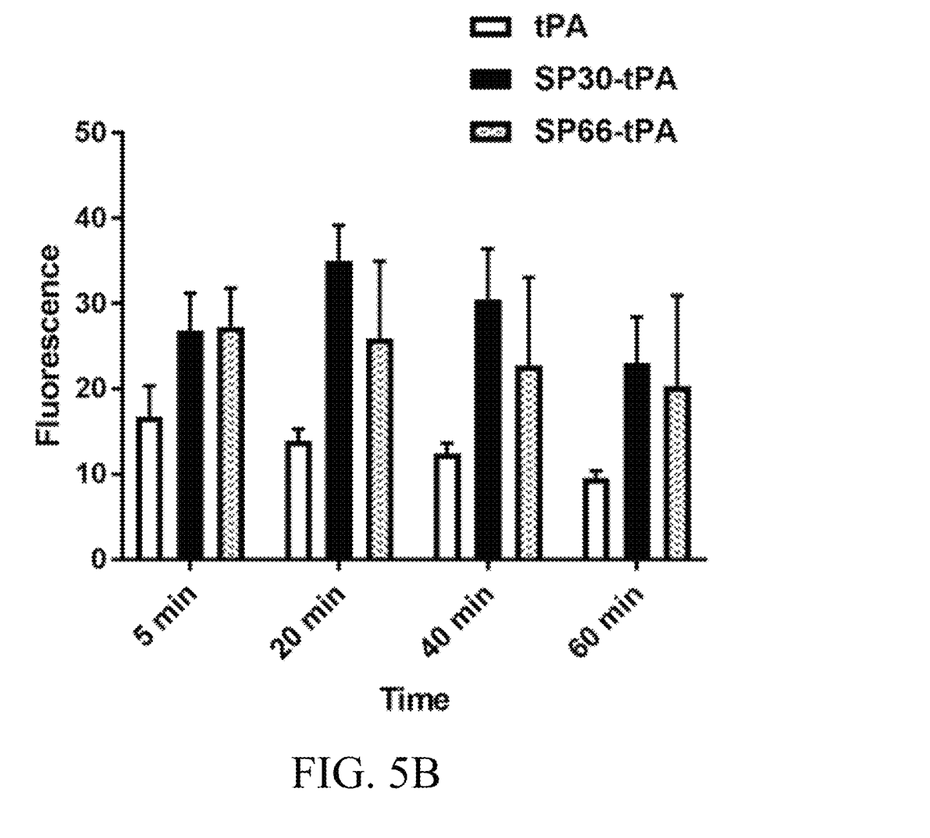
FIG. 5B is a histogram illustrating the quantification result of specified fusion proteins in induced thrombus. Fluorescence measurements of specified fusion proteins within the induced thrombus are plotted against time post-treatment.

Before live imaging of infrared fluorescence, mice with an induced thrombus were intravenously injected with dye-conjugated SP30-tPA and SP66-tPA (FIG. 5A). Images were acquired at several time-points post-injection. Dye-conjugated tPA (without thrombus binding peptide) was used as a negative control. The data indicated that the tPA control accumulated at the induced thrombus as soon as 5 minutes after injection, and the fluorescence intensity decreased by 50% in 1 hour (FIG. 5B). In contrast, the mice injected with thrombus-binding peptide-tPA fusion protein had two-fold higher fluorescence 5 minutes after injection compared to tPA, and the fluorescence remained similarly elevated 1 hour post-injection (FIG. 5B).

The data suggested that the SP30 and SP66 targeting peptides are effective tools to concentrate and maintain tPA at the thrombus site.

2.3 In Vivo MCAO Mouse Model

Figure 6:
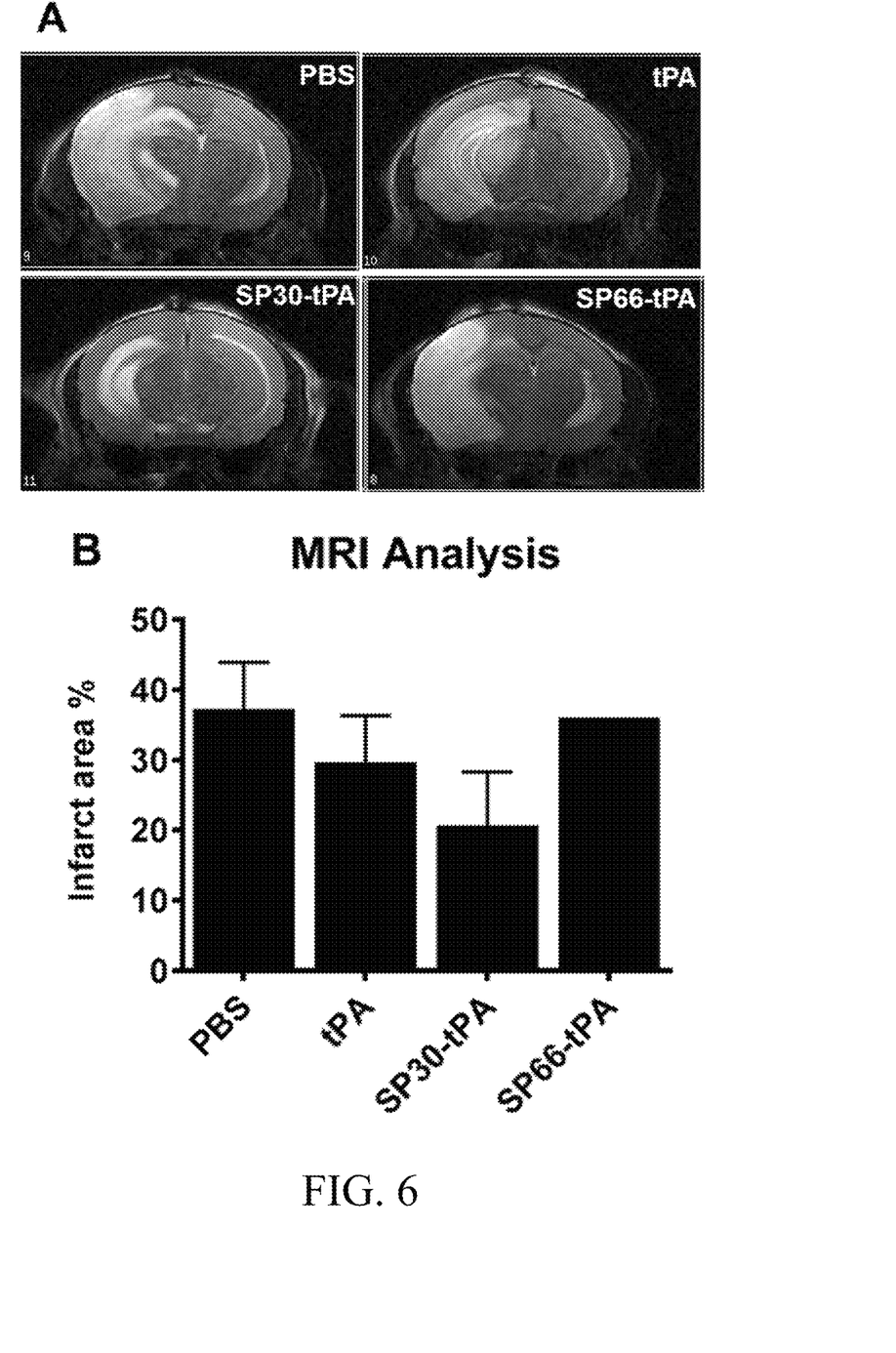
FIG. 6 depicts the therapeutic effect of specified fusion proteins in middle cerebral artery occlusion (MCAO) mouse model. Panel A are T2-weighted magnetic resonance images of MCAO mice injected with vehicle (PBS), tPA, SP30-tPA or SP66-tPA. White color in T2-weighted MRI indicates area of infarction. Panel B is a histogram illustrating the analysis result of infarction area in the brains of MCAO mice administered with specified treatments.

For the purse of examining whether the thrombus-binding peptide-tPA fusion proteins restored blood flow better than tPA in a stroke disease model, a murine MCAO model was employed in this example. MCAO was performed, and mice were treated with tPA or SP30/SP66-tPA fusion protein. According to the T2-weighted MRI of MCAO mouse brains 24 hour after drug administration, the cerebral infraction area of mice injected with SP30-tPA was lower compared to those of mice injected with control (PBS) or tPA alone (FIG. 6). These results suggested that targeting tPA to the thrombus can improve its efficacy against stroke-induced tissue damage.

In conclusion, the present disclosure provides three novel peptides respectively comprise the amino acid sequences of FQNEWFHNFLHD (SEQ ID NO: 1), TEANLSSWVFAR (SEQ ID NO: 2) and LQKNPFDLVQIL (SEQ ID NO: 3). According to examples of the present disclosure, each peptide is capable of specifically binding to thrombus, and accordingly, may serve as a targeting element for delivering a therapeutic agent (e.g., tPA) to the thrombus thereby improving the therapeutic safety and efficacy of the therapeutic agent.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A biomolecule comprising a synthetic peptide for targeting thrombus, wherein the synthetic peptide has the amino acid sequence of FQNEWFHNFLHD (SEQ ID NO: 1), TEANLSSWVFAR (SEQ ID NO: 2), or LQKNPFDLVQIL (SEQ ID NO: 3).

2. The biomolecule of claim 1, further comprising a therapeutic agent coupled to the synthetic peptide, wherein the therapeutic agent is an anticoagulant agent or a thrombolytic agent.

3. The biomolecule of claim 2, further comprising a linker comprising glycine (G) and serine (S) residues, wherein the therapeutic agent is coupled to the synthetic peptide via the linker.

4. The biomolecule of claim 2, wherein the anticoagulant agent is coumarin, warfarin, acenocoumarol, phenprocoumon, atromentin, phenindione, brodifacoum, difenacoum, heparin, fondaparinux, idraparinux, idrabiotaparinux, rivaroxaban, apixaban, edoxaban, betrixaban, darexaban, letaxaban, eribaxaban, hirudin, lepirudin, bivalirudin, argatroban, dabigatran, ximelagatran, batroxobin, hementin, coumadin, aspirin, ticlopidine, clopidogrel, or prasugrel.

5. The biomolecule of claim 2, wherein the thrombolytic agent is tissue plasminogen activator (tPA), staphylokinase, streptokinase, or urokinase.

6. The biomolecule of claim 5, wherein the tPA is reteplase, alteplase, tenecteplase, or lanoteplase.

7. The biomolecule of claim 2, further comprising a reporter molecule coupled to the synthetic peptide or the therapeutic agent, wherein the reporter molecule is a tag molecule, a radioactive molecule, a fluorescent molecule, a phosphorescent molecule, or a chemiluminescent molecule.

8. A pharmaceutical composition for treating a thromboembolism-related disease, comprising the biomolecule of claim 2, and a pharmaceutically acceptable excipient.

9. A method of treating stroke in a subject in need thereof, comprising administering to the subject an effective amount of the biomolecule of claim 2, wherein the therapeutic agent is a thrombolytic agent.

10. The method of claim 9, wherein the thrombolytic agent is tPA, staphylokinase, streptokinase, or urokinase.

11. The method of claim 10, wherein the tPA is reteplase, alteplase, tenecteplase, or lanoteplase.

12. The method of claim 9, wherein the subject is a human.

13. A method of treating stroke in a subject in need thereof, comprising administering to the subject an effective amount of the pharmaceutical composition of claim 8, wherein the therapeutic agent is a thrombolytic agent.

14. The method of claim 13, wherein the thrombolytic agent is tPA, staphylokinase, streptokinase, or urokinase.

15. The method of claim 14, wherein the tPA is reteplase, alteplase, tenecteplase, or lanoteplase.

16. The method of claim 13, wherein the subject is a human.

* * * * *